US011474120B2

(12) United States Patent
Kim et al.

(10) Patent No.: US 11,474,120 B2
(45) Date of Patent: Oct. 18, 2022

(54) SEPARABLE CASSETTE FOR MEASURING GLYCATED HEMOGLOBIN

(71) Applicant: GREEN CROSS MEDICAL SCIENCE, Yongin-si (KR)

(72) Inventors: Hyu Jeong Kim, Seoul (KR); Hyong Soo Kim, Yongin-si (KR); Dong Han Kim, Uiwang-si (KR); Eun Myung Shin, Suwon-si (KR); Jung Sub Shin, Ansan-si (KR); Soon Min Hong, Yongin-si (KR); Su Hyun Lee, Yongin-si (KR); Dong Cheol Choi, Yongin-si (KR)

(73) Assignee: GREEN CROSS MEDICAL SCIENCE, Yongin-si (KR)

( * ) Notice: Subject to any disclaimer, the term of this patent is extended or adjusted under 35 U.S.C. 154(b) by 424 days.

(21) Appl. No.: 16/337,721

(22) PCT Filed: Sep. 29, 2016

(86) PCT No.: PCT/KR2016/010875
§ 371 (c)(1),
(2) Date: Mar. 28, 2019

(87) PCT Pub. No.: WO2018/062587
PCT Pub. Date: Apr. 5, 2018

(65) Prior Publication Data
US 2019/0234981 A1   Aug. 1, 2019

(51) Int. Cl.
*G01N 35/04*   (2006.01)
*G01N 33/72*   (2006.01)
(Continued)

(52) U.S. Cl.
CPC .............. *G01N 35/04* (2013.01); *A61B 5/15* (2013.01); *B01L 3/502* (2013.01); *G01N 33/72* (2013.01);
(Continued)

(58) Field of Classification Search
None
See application file for complete search history.

(56) References Cited

U.S. PATENT DOCUMENTS

| 5,162,237 A | 11/1992 | Messenger et al. |
| 5,372,948 A | 12/1994 | Yip |

(Continued)

FOREIGN PATENT DOCUMENTS

| CN | 104897907 A | 9/2015 |
| CN | 105021544 A | 11/2015 |

(Continued)

OTHER PUBLICATIONS

International Search Report for PCT/KR2016/010875 dated Jun. 26, 2017 (PCT/ISA/210).

(Continued)

*Primary Examiner* — Kathryn Wright
(74) *Attorney, Agent, or Firm* — Sughrue Mion, PLLC

(57) ABSTRACT

The present invention relates to a separable cassette for measuring glycated hemoglobin. It is easy to use the separable cassette for measuring glycated hemoglobin of the present invention since a reagent is sequentially leaked during the rotation thereof. In addition, there is no need to shake the reagent beforehand, as the reagent without residual reagent is fully discharged by the rotation. Therefore, the measurement result is accurate because an error between the amount of the reagent used and the amount of sample blood is small.

10 Claims, 11 Drawing Sheets

(51) Int. Cl.
*B01L 3/00* (2006.01)
*A61B 5/15* (2006.01)
*G01N 35/00* (2006.01)

(52) U.S. Cl.
CPC .......... *G01N 33/723* (2013.01); *G01N 35/00* (2013.01); *B01L 2200/04* (2013.01); *B01L 2200/0615* (2013.01); *B01L 2200/16* (2013.01); *G01N 2035/0439* (2013.01); *G01N 2440/38* (2013.01)

(56) References Cited

U.S. PATENT DOCUMENTS

| | | | |
|---|---|---|---|
| 6,300,142 | B1 | 10/2001 | Andrewes et al. |
| 8,557,590 | B2 | 10/2013 | Bae et al. |
| 2007/0154351 | A1 | 7/2007 | Bae et al. |
| 2009/0093012 | A1 | 4/2009 | Bae et al. |
| 2010/0196999 | A1 | 8/2010 | Bae et al. |
| 2011/0104731 | A1 | 5/2011 | Teng et al. |
| 2013/0121898 | A1* | 5/2013 | Chen ............ B01L 3/502 422/554 |
| 2014/0127828 | A1 | 5/2014 | Hou et al. |
| 2015/0044764 | A1 | 2/2015 | Cha et al. |
| 2015/0147804 | A1 | 5/2015 | Cha et al. |
| 2016/0266099 | A1 | 9/2016 | Price et al. |
| 2018/0193841 | A1* | 7/2018 | Liu ............ G01N 33/54366 |
| 2019/0240667 | A1* | 8/2019 | Ledden ............ B01L 3/527 |
| 2019/0242911 | A1 | 8/2019 | Kim et al. |

FOREIGN PATENT DOCUMENTS

| | | |
|---|---|---|
| EP | 0 407 827 A2 | 1/1991 |
| EP | 2047909 A2 | 4/2009 |
| EP | 2047909 A3 | 8/2009 |
| JP | 3447360 B2 | 9/2003 |
| JP | 2009-300433 A | 12/2009 |
| JP | 2015-524566 A | 8/2015 |
| KR | 10-0798471 B1 | 1/2008 |
| KR | 10-0799354 B1 | 1/2008 |
| KR | 10-2010-0136744 A | 12/2010 |
| KR | 10-1069823 B1 | 10/2011 |
| KR | 10-2013-0119742 A | 11/2013 |

OTHER PUBLICATIONS

International Search Report for PCT/KR2016/012652, dated Jul. 24, 2017.

* cited by examiner

[Fig. 1]
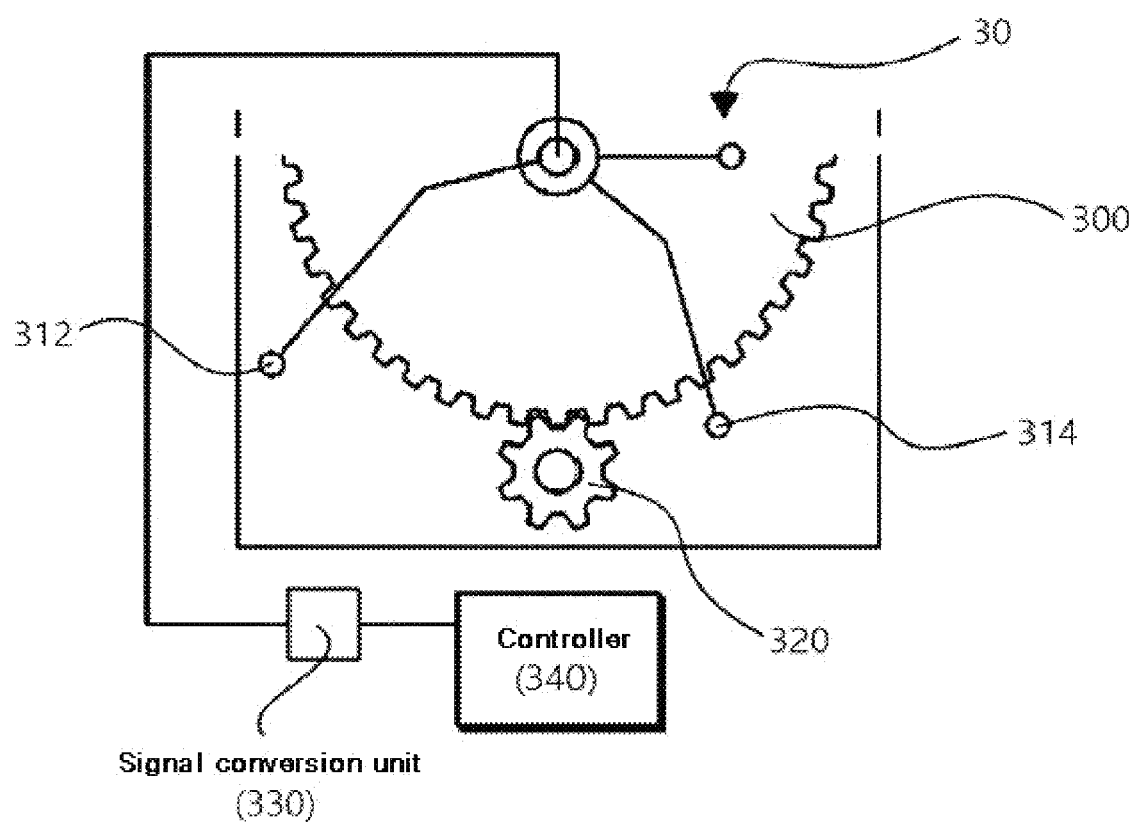

[Fig. 2]
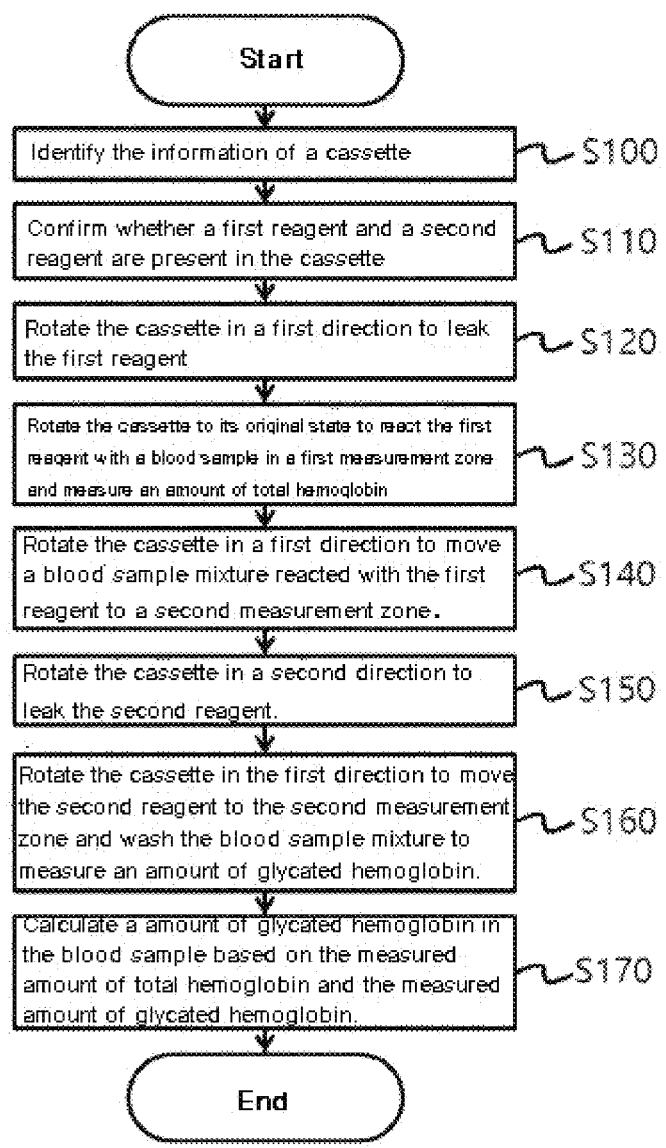

[Fig. 6]
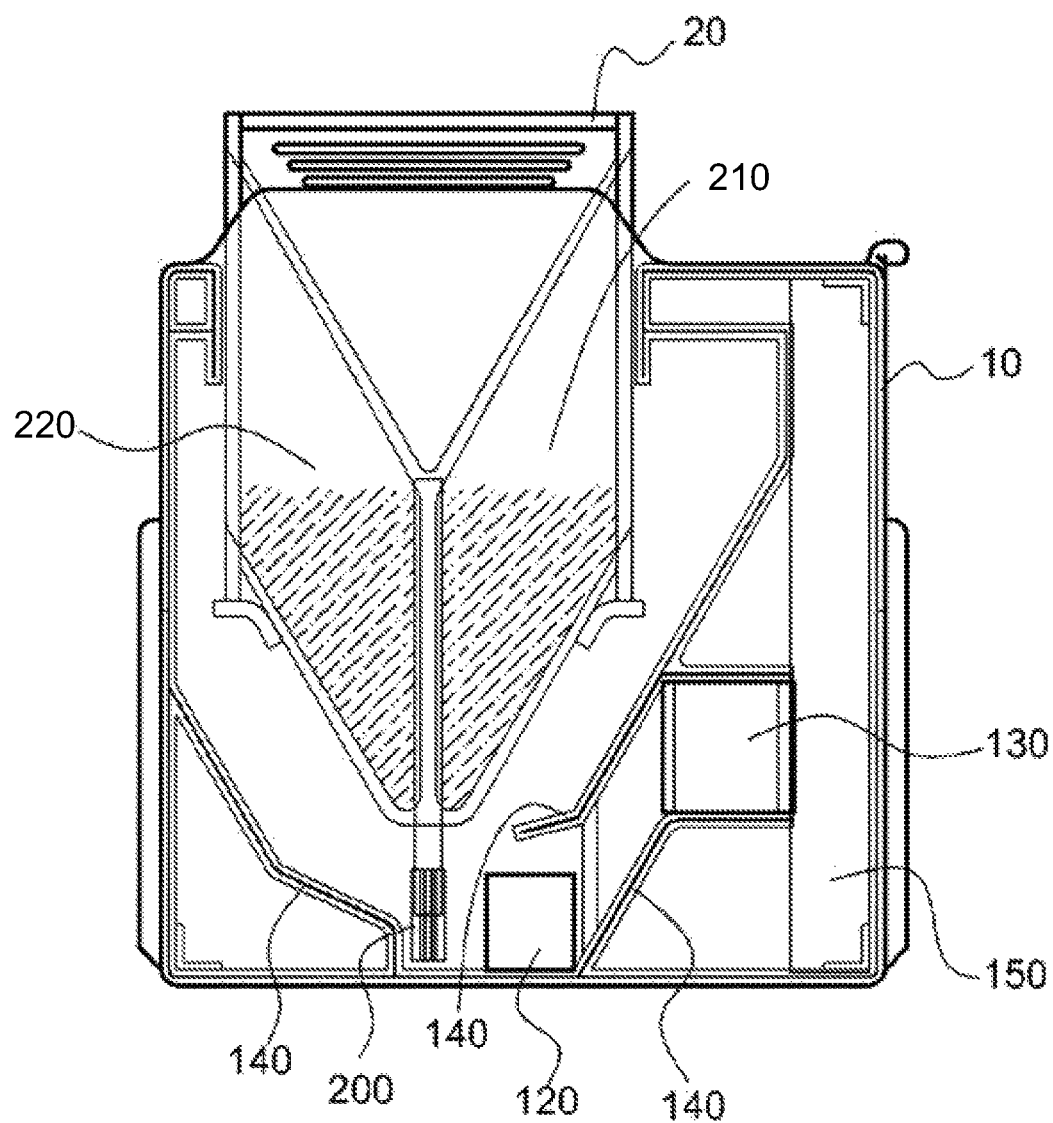

[Fig. 7]
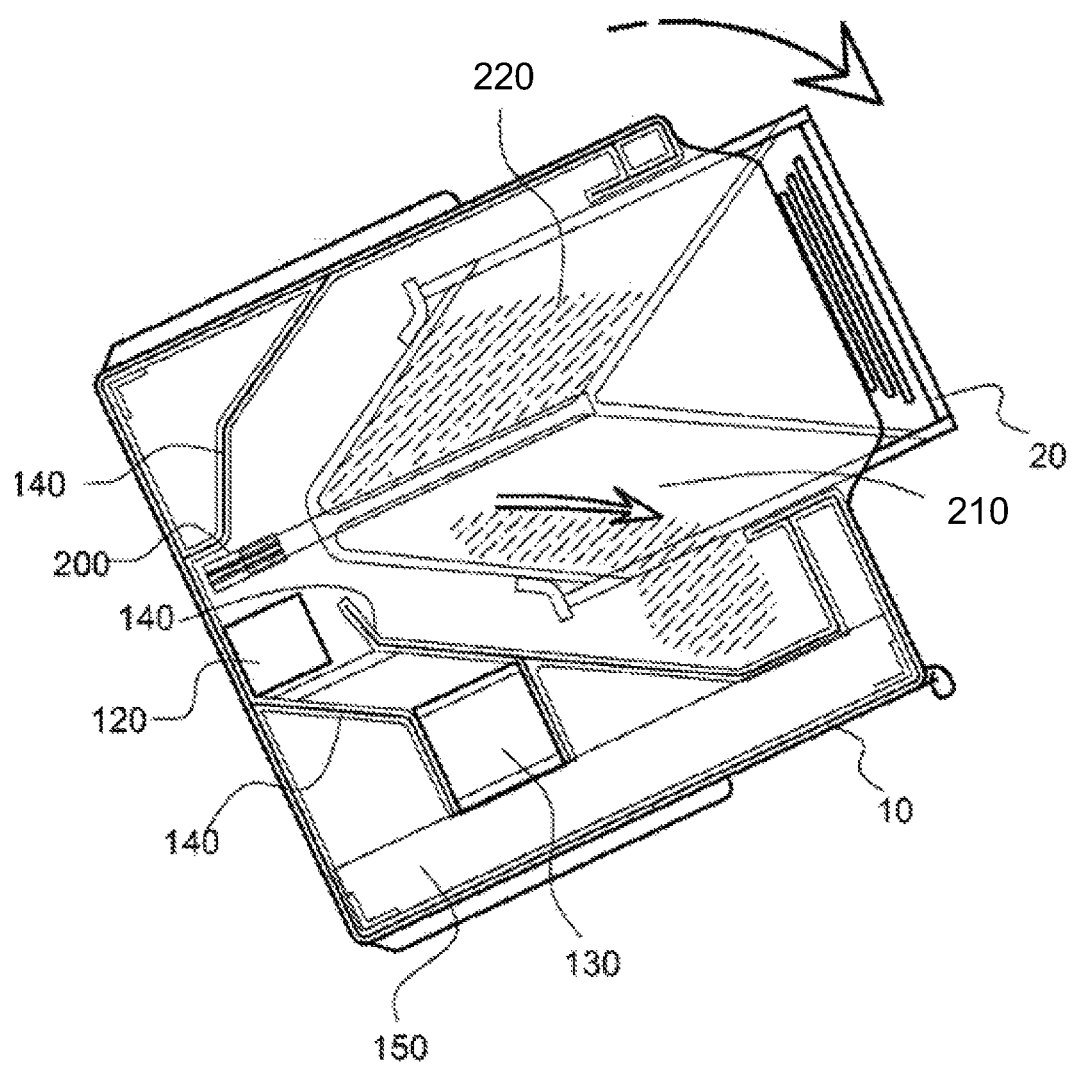

[Fig. 8]
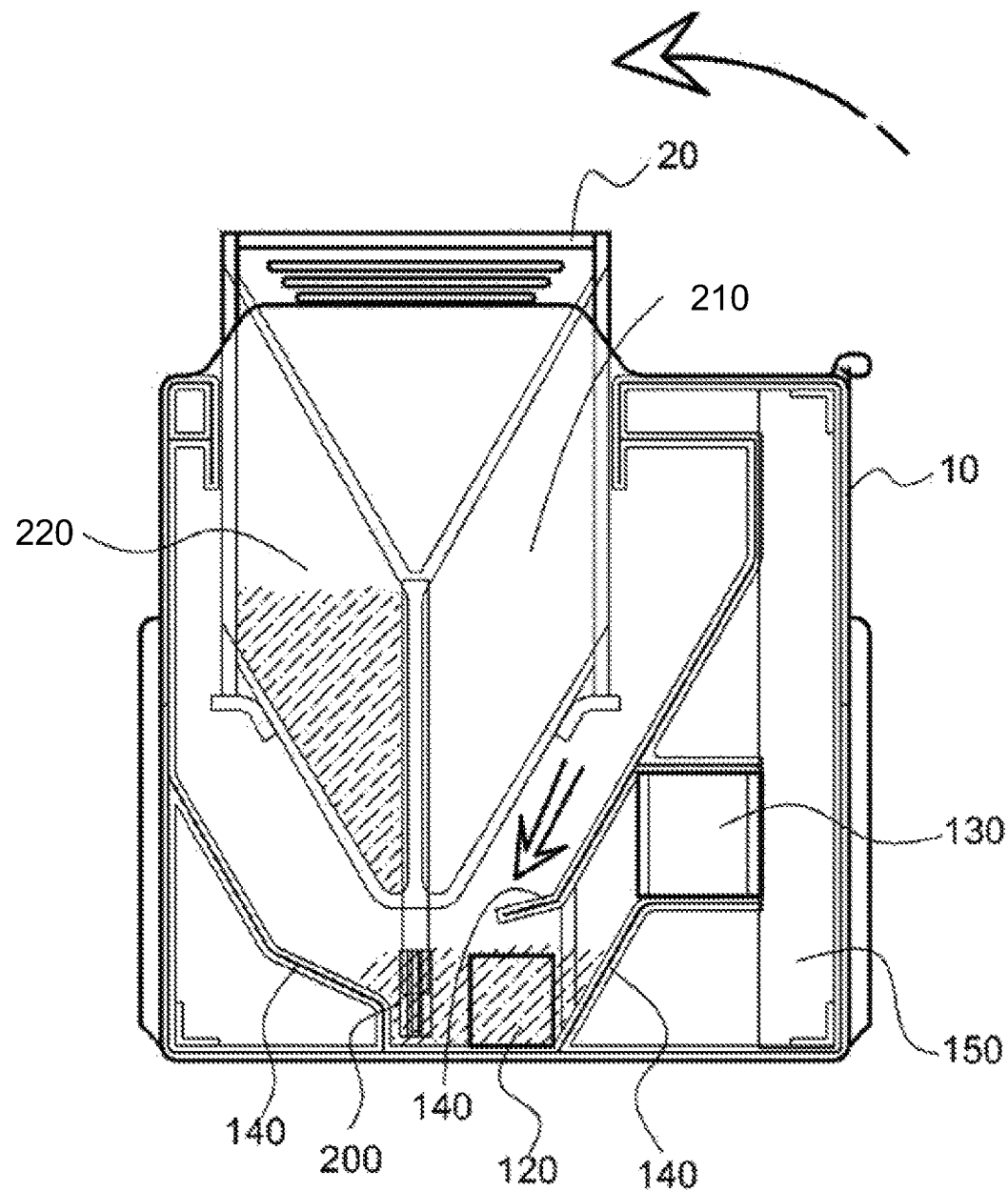

[Fig. 9]
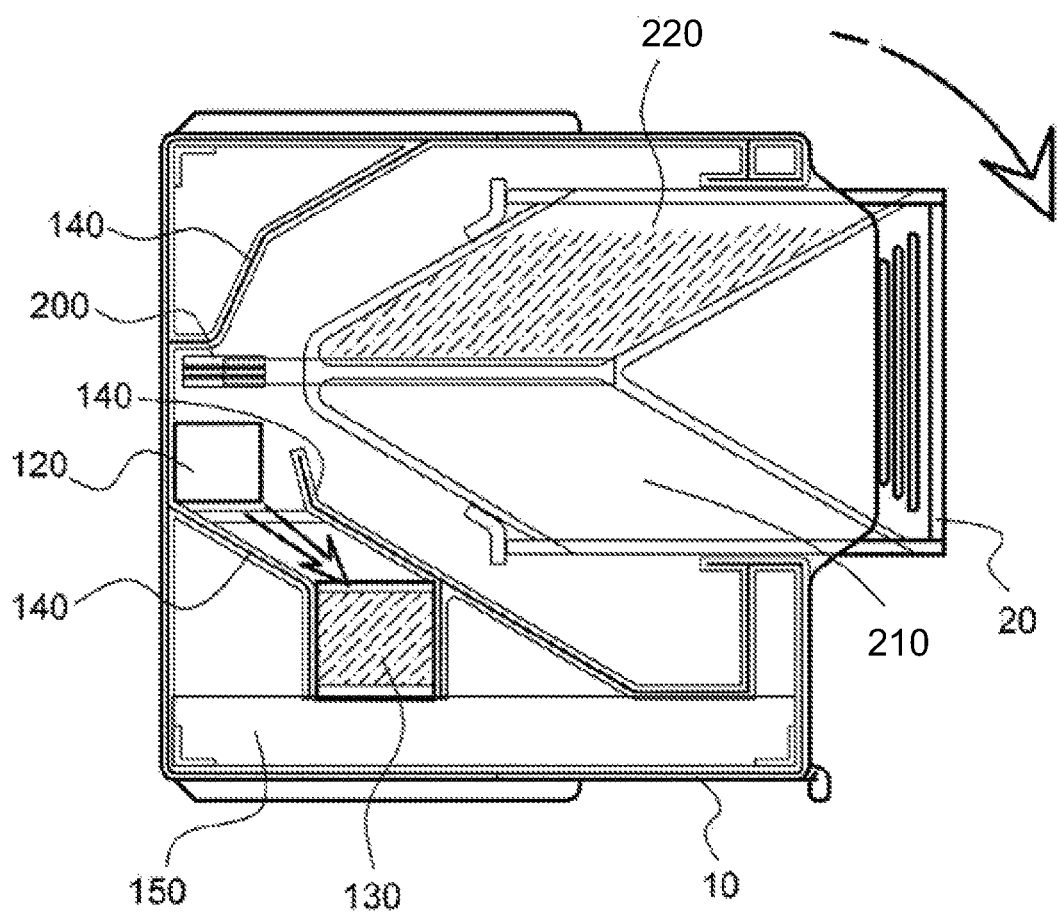

【Fig. 10】
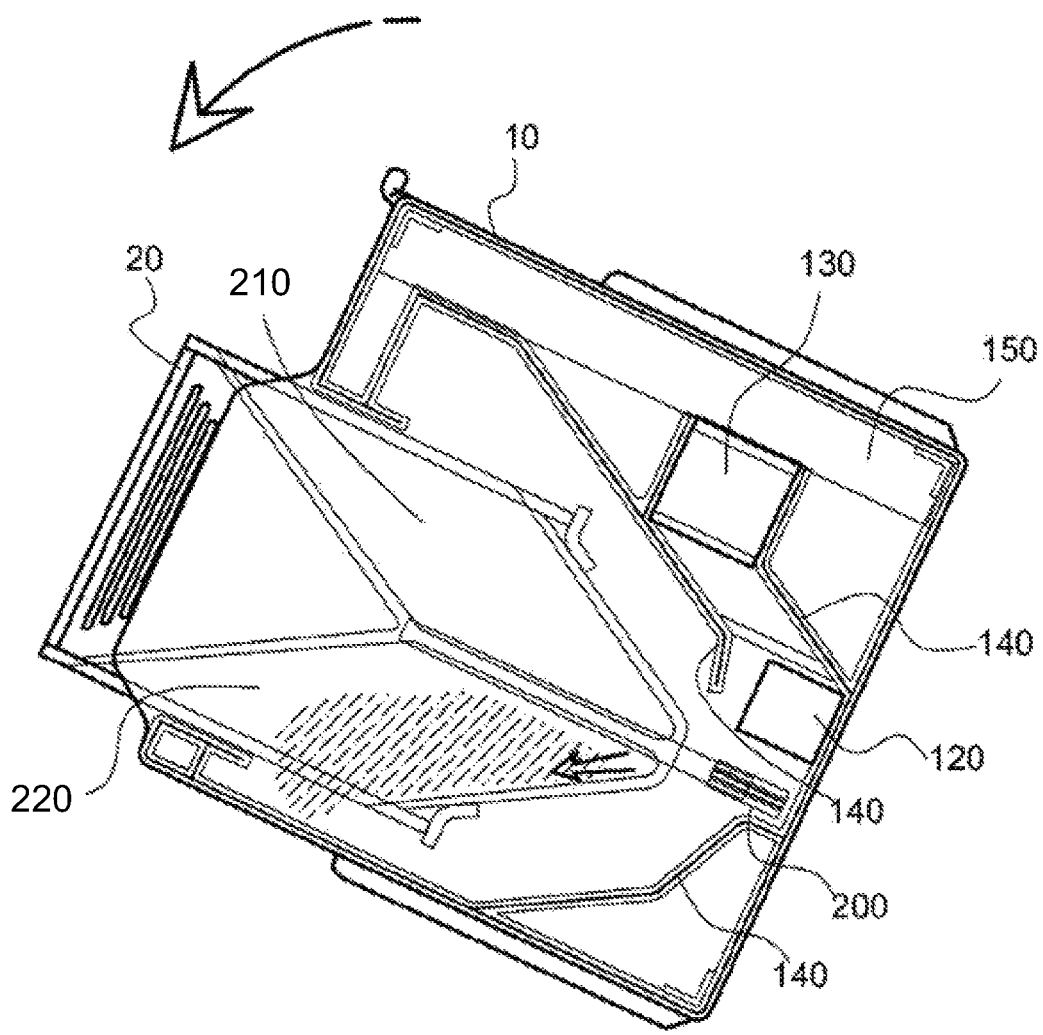

[Fig. 11]
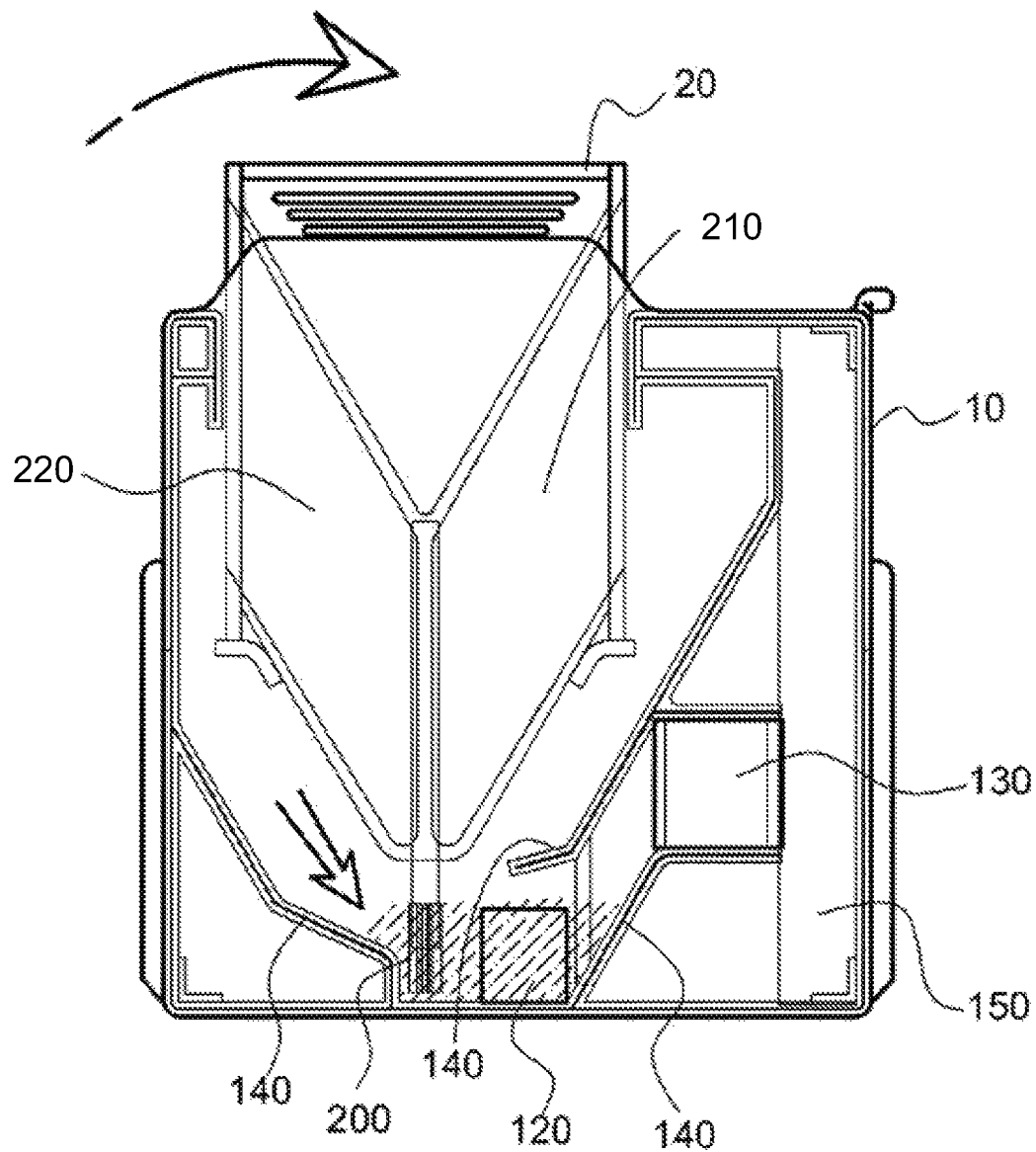

[Fig. 12]
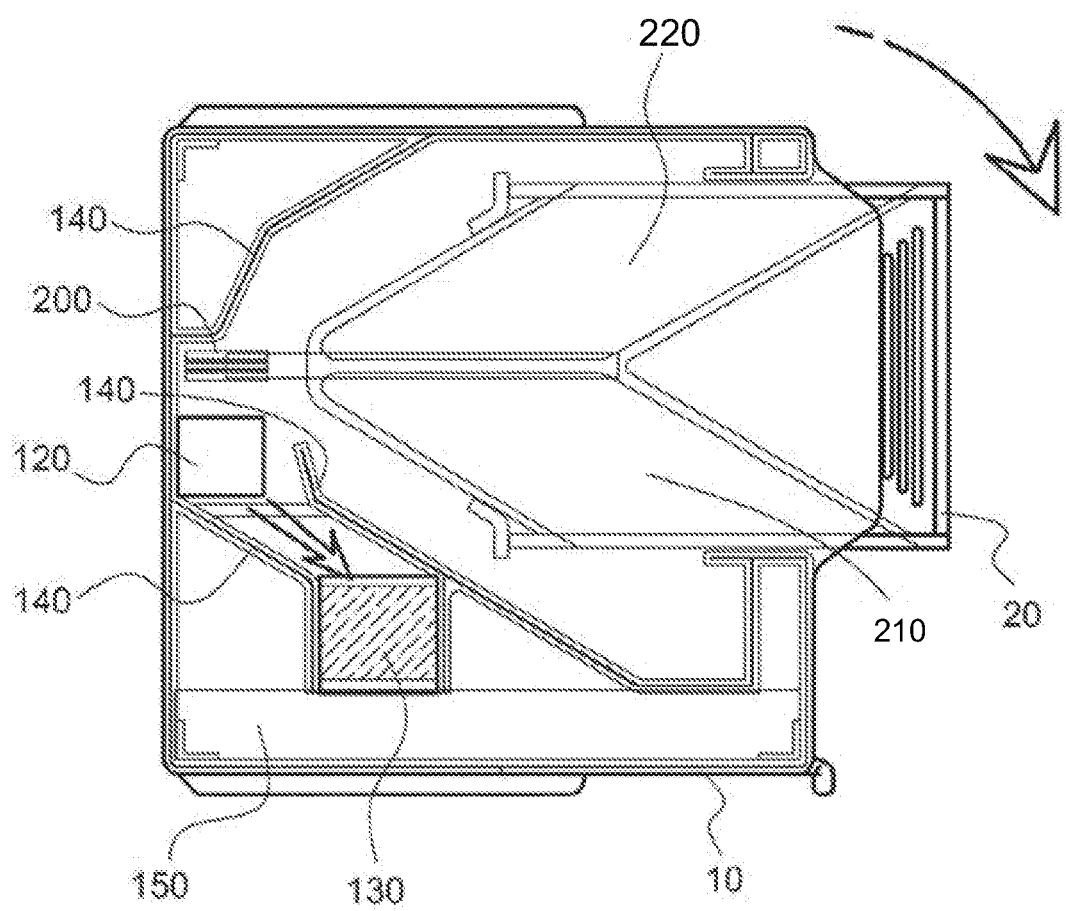

SEPARABLE CASSETTE FOR MEASURING GLYCATED HEMOGLOBIN

CROSS REFERENCE TO RELATED APPLICATIONS

This application is a National Stage of International Application No. PCT/KR2016/010875 filed Sep. 29, 2016.

TECHNICAL FIELD

The present invention relates to a separable cassette for measuring glycated hemoglobin.

BACKGROUND ART

In the fields of medical diagnosis or drug-based therapy, the concentration measurement of analytes of anesthetics or harmful chemicals has recently been useful in medical or environmental fields. Above all, the concentration measurement of biological samples used in the fields of medical diagnosis and therapy is increasingly drawing interest along with an increase in human desire to be free from various diseases. Particularly, with regard to diabetes, the glycated hemoglobin test capable of measuring blood sugar allows a relatively long-term average value of the blood sugar to be detected by one-time measurement, and thus has an increasing interest.

Hemoglobin A1c (HbA1c) is also called glycated hemoglobin, and is present in human red blood cells as a part of hemoglobin. When a concentration of blood sugar (glucose) in the blood rises, a glucose moiety in the blood binds to hemoglobin. This hemoglobin conjugated with glucose is referred to as glycated hemoglobin. Blood sugar levels can be determined by this glycated hemoglobin test, which has an advantage in that it can be conducted by collecting blood regardless of the meal time.

Meanwhile, U.S. Pat. No. 6,300,142 discloses an apparatus for reacting a test sample with a first reactant in a first inlet port and sequentially reacting the reacted test sample with a second reactant in a second inlet port to measure the analyte present in the test sample. In this case, the measurement of the analyte has to be conducted periodically and sequentially. Further, a user has to intervene in the measuring process in such a manner that he or she injects the test sample sequentially to react the test sample with other materials. Furthermore, since beads conjugated with the glycated hemoglobin have to be filtered once, the measuring process is complicated and takes a long time. That is, since the conventional measuring process requires the user's direct intervention in various processing steps, the user may feel inconvenient. Also, the user's direct intervention makes the measuring process more complicated, thereby further increasing the measuring time.

Korean Patent No. 10-0798471 also discloses a cassette characterized by comprising: a first receiving zone for receiving a first reagent; a second receiving zone for receiving a second reagent; a reaction zone in which the blood sample reacts with the first reagent or the second reagent; and a measurement zone for measuring an amount of total hemoglobin or an amount of glycated hemoglobin in a blood sample, wherein the reaction zone and the measurement zone are formed so as to be divided according to a rotation angle of the cassette. However, in the case of this cassette, there is a possibility that some of the two reagents may be mixed in the process of injecting the first reagent and the second reagent into the first receiving zone and the second receiving zone, respectively. Further, since the manufacturing of the cassette is performed by the process of attaching the upper plate to the structure frame in which the internal structure is formed, the movement of the reagents due to the capillary phenomenon may occur along the minute gap present at the adhesion region between the upper plate and the structure frame, thereby causing an error in the measurement results. Thus, it is preferable that the reagents remain in the receiving zones of the cassette for a minimum amount of time. When a blood sample is injected into the cassette from a cartridge including a blood sampling unit configured to contain the blood sample, the amount of the blood sample to be collected is not constant. Further, if the amount of the collected sample exceeds the measurement limit amount, there is a problem that an error may be caused in the measurement results. Furthermore, there is also an inconvenience that the reagents must be mixed well by shaking the cartridge sufficiently before fastening the cartridge to the measurement cassette. There is also a limit in which the reagents remain after use. Therefore, there is a demand for a cassette and a cartridge which are easy to use and can provide accurate measurement results.

PRIOR ART DOCUMENTS

Patent Documents

Korean Patent No. 10-1069823, entitled "cassette for measuring the concentration of glycosylated Hemoglobin"
Korean Patent No. 10-0799354, entitled "reagent vessel"

DISCLOSURE

Technical Problem

The present inventors have completed the present invention based on the idea that when a cassette for measuring glycated hemoglobin is manufactured in the separate form and then the cassette rotates, the reagents automatically leak out sequentially in the course of the rotation of the cassette, so that it is easy to use and the reagents are fully discharged without any residual reagents, thereby outputting the accurate measurement results.

Accordingly, it is an object of the present invention to provide a separable cassette which can more effectively measure glycated hemoglobin by inducing each reagent to leak sequentially in accordance with the rotation of the cassette.

Technical Solution

In order to achieve the above purpose, the present invention provides a separable cassette for measuring glycated hemoglobin, comprising:

a cartridge which includes a first storage zone for storing a first reagent, a second storage zone for storing a second reagent, and a blood sampling unit capable of injecting a blood sample into the cassette, and is inserted into the cassette;

a first measurement zone in which the blood sample reacts with the first reagent to measure an amount of total hemoglobin; and a second measurement zone in which the reacted blood sample reacts with the second reagent to measure an amount of glycated hemoglobin, wherein as the cassette rotates by a predetermined angle or more, the first reagent or the second reagent leaks from the first storage zone or the second storage zone, or moves into the first measurement zone or the second measurement zone.

In an embodiment of the present invention, the first reagent includes a hemolysate and a glycated hemoglobin binding material-bead which selectively reacts with the glycated hemoglobin, wherein the bead may include one or more selected from the group consisting of an agarose bead, a sepharose bead, a latex bead, and a glass bead.

In an embodiment of the present invention, the glycated hemoglobin binding material may include one or more selected from the group consisting of a boronic acid, concanavalin A, and an antibody.

In an embodiment of the present invention, the blood sampling unit may be in the form of a capillary.

In an embodiment of the present invention, the cassette may further comprise an insertion guide unit for guiding an insertion direction when the cartridge is inserted into the cassette.

In an embodiment of the present invention, the cartridge further comprises a leakage preventing unit which is disposed at one end of the first storage zone and the second storage zone, respectively, to prevent the first reagent and the second reagent from leaking out, and can be removed from the cartridge when the cartridge is inserted into the cassette.

In an embodiment of the present invention, the leakage preventing unit may be a foil cover or a foil tap.

In an embodiment of the present invention, the leakage preventing unit is removed by a removing part which is disposed in the inlet port of the cassette and may comprise a protruding part so that the leakage preventing unit is caught and removed.

In an embodiment of the present invention, the first reagent may leak from the first storage zone when the cassette rotates 10-130° in a first direction based on its original state.

In an embodiment of the present invention, the second reagent may leak from the second storage zone when the cassette rotates 10-130° in a second direction based on its original state.

In an embodiment of the present invention, the cassette may further comprise a delivery guide unit for guiding for the blood sample, the first reagent, or the second reagent, to move to the first measurement zone or the second measurement zone.

In an embodiment of the present invention, the cassette may further comprise a sample absorption unit which is located at one end of the second measurement zone to absorb the measured blood sample and sample.

In an embodiment of the present invention, the cassette may further comprise an optical window from which light received through an external optical sensor is reflected.

Advantageous Effects

The separable cassette for measuring glycated hemoglobin according to the present invention is easy to use because the reagents leak out sequentially in the course of its rotation, the reagents are fully discharged without any residual reagents by the rotation, and the reagents do not mix with each other. Therefore, the measurement results are accurate because there is little error in the amount of the reagents used and the amount of blood samples.

BRIEF DESCRIPTION OF DRAWINGS

FIG. 1 is a schematic view showing an exemplary device for measuring glycated hemoglobin in which the separable cassette for measuring glycated hemoglobin according to the present invention can be used.

FIG. 2 is a flowchart illustrating a method of measuring glycated hemoglobin using the cassette according to an embodiment of the present invention.

FIGS. 6 to 12 are exemplary views showing the process in which the separable cassette for measuring glycated hemoglobin according to the present invention rotates to measure the glycated hemoglobin.

BEST MODE

Figure 3A:
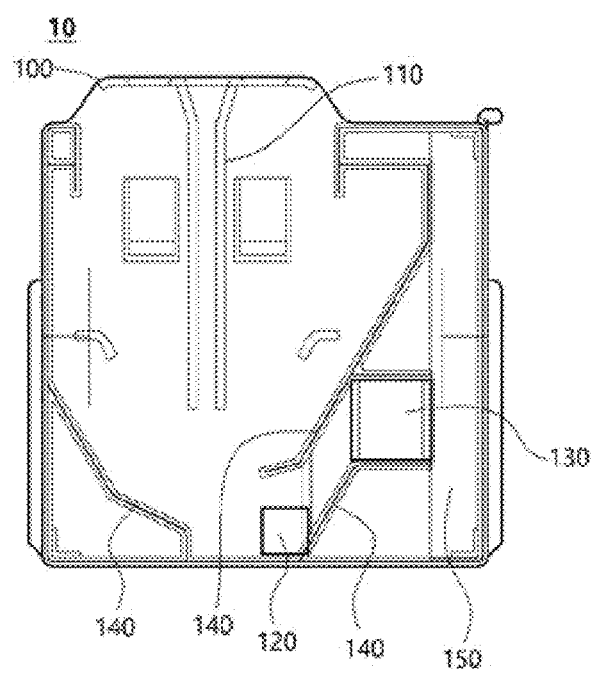
FIG. 3(a) and FIG. 3(b) illustrate an external appearance and an internal appearance of the cassette, respectively, according to an embodiment of the invention.

Hereinafter, preferred examples according to the present invention will be described in detail with reference to the accompanying drawings. However, the present invention is not limited to the examples described herein and may be embodied in other forms.

As used herein, terms "rotation in a first direction" and "rotation in a second direction" refer to rotation in mutually opposite directions. For example, if the first direction is clockwise, then the second direction automatically means counterclockwise, or vice versa. The term "original state of the cassette" means that the cassette stands upright on a flat ground without rotation or tilt, and may include a state of tilting about −35 to 30° relative to the ground depending on the shape of the cartridge.

In addition, the separable cassette according to the present invention has a form in which the cartridge and the cassette are separated before the measurement of the glycated hemoglobin. In the measurement of glycated hemoglobin, the measurement is performed while the cartridge is inserted into the cassette including the first reagent, the second reagent, and the blood sample.

The present invention provides a separable cassette for measuring glycated hemoglobin 10, comprising:

a cartridge 20 which includes a first storage zone 210 for storing a first reagent, a second storage zone 220 for storing a second reagent, and a blood sampling unit 200 capable of injecting a blood sample into the cassette 10, and is inserted into the cassette 10;

a first measurement zone 120 in which the blood sample reacts with the first reagent to measure an amount of total hemoglobin; and a second measurement zone 130 in which the reacted blood sample reacts with the second reagent to measure an amount of glycated hemoglobin; and wherein as the cassette 10 rotates by a predetermined angle or more, the first reagent or the second reagent leaks from the first storage zone 210 or the second storage zone 220, or moves into the first measurement zone 120 or the second measurement zone 130.

The first storage zone 210 and the second storage zone 220 may store at least one reagent, respectively.

The first storage zone 210 may store the first reagent. At this time, the first reagent can react with the blood sample. For example, the first reagent may include a hemolysate for hemolyzing the blood sample and a glycated hemoglobin binding material-bead which selectively reacts with the glycated hemoglobin.

The hemolysate may be, for example, a buffer solution containing a surfactant, such as N-2-Hydroxyethylpiperazine-N'-2-ethanesulfonic Acid (HEPES; pH 8.1). The blood sample hemolyzed by the hemolysate may include both a non-glycated hemoglobin and a glycated hemoglobin.

The glycated hemoglobin binding material may be a material capable of specifically binding to the glycated hemoglobin. For example, the glycated hemoglobin binding material may include one or more selected from the group consisting of a boronic acid (BA), concanavalin A (lectin), and an antibody.

The bead may include one or more selected from the group consisting of a polymer polysaccharide support such as agarose, cellulose, or sepharose; a latex bead such as polystyrene, polymethylmethacrylate, or polyvinyltolune; and a glass bead.

It is preferable that the particle diameter of the glycated hemoglobin binding material-bead is selected in consideration with the precipitation time of the glycated hemoglobin binding material-bead conjugated with glycated hemoglobin after reaction, and the reactivity with the glycated hemoglobin.

In summary, the first reagent may include the hemolysate for hemolyzing the blood sample and the glycated hemoglobin binding material-bead which selectively reacts with the glycated hemoglobin. The first reagent hemolyzes the blood sample, and then the amount of total hemoglobin is measured after about 10-20 seconds and the reaction of the first reagent and the glycated hemoglobin is performed for about 30-60 seconds.

The second storage zone 220 may store the second reagent. The second reagent may be a reagent including a washing solution which is able to wash off a mixture of the first reagent and the blood sample.

Most of hemoglobin (Hb) present in red blood cells of a blood sample is non-glycated hemoglobin (Ao). Only 4-14% of the non-glycated hemoglobin reacts with glucose to become glycated hemoglobin (HbA1c). Accordingly, the glycated hemoglobin binding material-beads in the first reagent which has reacted with the blood sample include non-glycated hemoglobin as well as glycated hemoglobin. Therefore, in order to measure only the glycated hemoglobin in the blood sample, it is needed to remove the non-glycated hemoglobin from the glycated hemoglobin binding material-beads. To this end, it is preferable that the second reagent includes a washing solution which is able to wash off the non-glycated hemoglobin from the glycated hemoglobin binding material-beads to enable the measurement of glycated hemoglobin.

In addition, as the cassette 10 rotates by a predetermined angle or more, the first reagent or the second reagent leaks from the first storage zone 210 or the second storage zone 220, or may move into the first measurement zone 120 or the second measurement zone 130.

To this end, for example, the first storage zone 210 and the second storage zone 220 may be formed such that the first reagent or the second reagent does not leak out until the cassette 10 rotates by a predetermined angle or more. According to the separable cassette 10 of the present invention, even if the cartridge 20 comprising the first storage zone 210 and the second storage zone 220 is inserted into the cassette 10, the first reagent and the second reagent do not leak out in its original state. The first reagent or the second reagent may leak out sequentially only when the cassette 10 into which the cartridge 20 is inserted rotates by a predetermined angle or more. Therefore, a leakage hole, which is a passage through which the reagent leaks out, may be formed on the upper side of the first storage zone 210 and the second storage zone 220. Also, the leakage hole may be formed on the opposite side of the upper of each storage zone so that as the cassette 10 rotates in the opposite direction, the first reagent and the second reagent may independently leak out.

The blood sample, the first reagent, and the second reagent, which have leaked into the cassette 10 according to the rotation of the cassette 10 may also move independently from the cassette 10 to the measurement zone in accordance with the rotation of the cassette 10.

The first measurement zone 120 is a region in which the blood sample and the first reagent react and simultaneously measures the amount of total hemoglobin in the blood sample reacted with the first reagent. In the first measurement zone 120, the amount of total hemoglobin in the blood sample can be measured by an optical reflectometry technique. For example, the optical reflectometry technique utilizes the characteristic that hemoglobin specifically absorbs an optical signal of a specific frequency. The concentration of total hemoglobin can be measured by relatively measuring the intensity or tone of light by the characteristic of hemoglobin.

The second measurement zone 130 is a region into which after the blood sample are mixed with the first reagent and the amount of total hemoglobin is measured in the first measurement zone 120, the blood sample mixture that has reacted with the first reagent moves in accordance with the rotation of the cassette 10, as well as a region in which the blood sample mixture reacts with the second reagent and the amount of glycated hemoglobin is measured. The measurement principle may be the same as that of the first measurement region 120. Here, the term "reaction" refers to a comprehensive reaction including not only a chemical reaction but also washing, bonding, agitation, etc.

The blood sampling unit 200 may be in the form of a capillary.

It is so that the blood sample to be measured is suck by the form of a capillary of the blood sampling unit 200. Particularly, the inside diameter of the tip of the blood sampling unit 200 is smaller than that of the remaining portion so that the capillary phenomenon is easily generated.

On the other hand, when the blood sample is injected into the cassette 10 from the blood sampling unit 200, if the amount of the blood sample to be sampled is not constant or exceeds the measurement limit amount, it may lead to an error in the result value. If an excessive amount of blood is contained in the blood sampling unit 200, the measuring device may deviate from the measurable range to obtain an excessive value. In the case of, for example, Clover A1c, available from Infopia Co., Inc., a measurable total hemoglobin level is 7-20 g/dl, and if excess blood is injected, the device recognizes that the hemoglobin level is out of the measurable range, thereby resulting in displaying a measured value higher than the normal value.

Therefore, the form of the blood sampling unit 200 is important. The tip of the blood sampling unit 200 includes a gap formed in parallel to the center, the width of the tip is narrowed toward the end of the tip, and the gap formed inside forms a groove close to the curve.

The amount of blood required for the measurement is preferably about 2.5-5.5 ul. The blood sampling unit 200 according to the present invention may contain about 3 ul of blood and its specific form prevents the excessive blood from sticking together to the blood sampling unit 200.

In an embodiment of the present invention, the cassette 10 may further comprise an insertion guide unit 110 for guiding an insertion direction when the cartridge 20 is inserted into the cassette 10.

The first storage zone 210 is preferably inserted into the cassette 10 so as to be closer to the first measurement zone 120 and the second measurement zone 130 than the second storage zone 220. The insertion guide unit 110 may be a concavo-convex shape formed on the inner surface of the cassette 10 so that the cartridge 20 can be inserted into the cassette 10 only in one direction by the insertion guide unit 110 and cannot be inserted upside down.

In an embodiment of the present invention, the cartridge 20 further comprises a leakage preventing unit 230 which is disposed at one end of the first storage zone 210 and the second storage zone 220, respectively, to prevent the first reagent and the second reagent from leaking out, and can be removed from the cartridge 20 when the cartridge 20 is inserted into the cassette 10.

The leakage preventing unit 230 may be formed at one end, preferably the upper side, of the first storage zone 210 and the second storage zone 220, respectively, and may seal the first reagent and the second reagent stored in the storage zones from the outside. The leakage preventing unit 230 may be caught and removed or damaged by the removing part 100 when the cartridge 20 is inserted into the cassette 10. The leakage preventing unit 230 may be a foil cover or a foil tab and may be a member that is not corroded or damaged from the reagents.

In an embodiment of the present invention, the leakage preventing unit 230 is removed by the removing part 100 which is disposed in the inlet port of the cassette 10 and may have a protruding part so that the leakage preventing unit 230 can be caught and removed.

The leakage preventing unit 230 is automatically removed by the removing part 100 when the cartridge 20 is inserted into the cassette 10, and the removing part 100 may have a suitable protruding shape so that the leakage preventing unit 230 can be caught and removed.

In an embodiment of the present invention, the first reagent may leak from the first storage zone 210 when the cassette 10 rotates 10-130° in the first direction based on its original state.

In an embodiment of the present invention, the second reagent may leak from the second storage zone 220 when the cassette 10 rotates 10-130° in the second direction based on its original state.

The rotation in the first direction and the rotation in the second direction mean rotation in mutually opposite directions. Even if the leakage preventing unit 230 is removed, the first reagent or the second reagent may not leak until the cassette 10 rotates. When the cassette 10 rotates 10-130° in the first direction or the second direction after the leakage preventing unit 230 is removed, the first reagent or the second reagent may leak through the leakage holes formed on the upper sides of the storage zones. For example, when the cassette 10 rotates 10-130° in the first direction, only the first reagent may leak, but the second reagent does not leak. Conversely, when the cassette 10 rotates 10-130° in the second direction, only the second reagent may leak, but the first reagent does not leak.

In an embodiment of the present invention, the cassette 10 may further comprise a delivery guide unit 140 for guiding the blood sample, the first reagent, or the second reagent, to move to the first measurement zone 120 or the second measurement zone 130.

The delivery guide unit 140 is a concavo-convex shape formed inside the cassette 10 and guides so that according to the rotation of the cassette 10, the first reagent leaking from the first storage zone 210 may move to the first measurement zone 120, a mixture of the blood sample and the first reagent from the first measurement zone 120 may move to the second measurement zone 130, and the second reagent leaking from the second storage zone 220 may move to the second measurement zone 130.

In an embodiment of the present invention, the cassette 10 may further comprise a sample absorption unit 150 which is located at one end of the second measurement zone 130 to absorb the measured blood sample and the sample. The sample absorption unit 150 absorbs the measured blood sample mixture to prevent the blood sample mixture from leaking out. For example, in order to measure the amount of glycated hemoglobin, the sample absorption unit 150 may absorb non-glycated hemoglobin and the remaining materials except for glycated hemoglobin binding material-beads conjugated with glycated hemoglobin, present in the second measurement zone 130. The sample absorption unit 150 may be disposed on the side of the second measurement zone 130. In an embodiment of the present invention, the sample absorption unit 150 may include, but is not limited to, an absorbent pad.

In an embodiment of the present invention, the cassette 10 may further comprise an optical window 160 from which light received from an external optical sensor is reflected. The external optical sensor is preferable located at the device for measuring glycated hemoglobin, into which the reaction cassette 10 is inserted.

In accordance with an embodiment of the present invention, an exemplary device for measuring glycated hemoglobin 30 in which a separable cassette for measuring glycated hemoglobin 10 may be used is shown in FIG. 1.

Referring to FIG. 1, the cassette 10 in which the cartridge 20 of the present invention is incorporated is inserted into a device for measuring glycated hemoglobin 30. At this time, the device for measuring glycated hemoglobin 30 may rotate the cassette 10 clockwise or counterclockwise according to a certain pattern. The rotation of the cassette 10 causes the first reagent or the second reagent to leak sequentially into the cassette 10, respectively, to be stirred together with the blood sample, and to move into the first measurement zone 120 or the second measurement zone 130 so that the measurement can be performed. The device for measuring glycated hemoglobin 30 can measure the amount of glycated hemoglobin using an optical reflectometry technique.

For example, when the amount of glycated hemoglobin in a blood sample is measured, a characteristic that hemoglobin specifically absorbs an optical signal of a specific frequency is utilized. At this time, it is preferable that the device for measuring glycated hemoglobin 30 measures the amount of glycated hemoglobin using a light-receiving element and a light-emitting element such as a photo diode.

Referring to FIG. 1, the device for measuring glycated hemoglobin 30 may comprise a cassette 10 accommodation part 300, a cassette 10 check sensor 312, a measurement sensor 314, a driving unit 320, a signal conversion unit 330, and a controller 340.

The cassette 10 accommodation part 300 has a space into which the cassette 10 is inserted. It is preferable that the cassette 10 accommodation part 300 has a sufficient space so that the cassette 10 may rotate clockwise or counterclockwise without any interruption.

The cassette 10 check sensor 312 may confirm whether the solution containing the reagents such as the first reagent and the second reagent in the cassette 10 is properly present in the first storage zone 210 and the second storage zone 220. The cassette 10 check sensor 312 confirms detection of reagents by an absorption photometry method using an optical sensor that emits an optical signal by a light-emitting element and receives the optical signal that has passed through the cassette 10 by a light-receiving element. That is, the cassette 10 check sensor 312 outputs a light-emitting control signal to the light-emitting element and converts an optical signal received from the light-receiving element into an electrical signal, thereby being able to detect whether the first reagent and second reagent are properly present.

In other words, the light-emitting element emits an optical signal having a specific wavelength. For example, when the amount of glycated hemoglobin is to be measured, the hemoglobin in the blood sample may emit an optical signal having a wavelength of about 400-600 nm in which the hemoglobin specifically shows absorption. The light-receiving element receives an optical signal which is emitted from the light-emitting element and passes through the cassette 10.

The measurement sensor 314 measures the amount of total hemoglobin and the amount of glycated hemoglobin which are contained in the second measurement zone 130 of the cassette 10. At this time, by outputting a light-emitting control signal to the light-emitting element and converting an optical signal inputted from the light-receiving element into an electrical signal, the amount of total hemoglobin and the amount of glycated hemoglobin which are contained in the cassette 10 can be measured.

The driving unit 320 applies an external power to the cassette 10. For example, the driving unit 320 may be a motor. The cassette 10 may rotate according to a predetermined rule by the external power, and the rotation angle may freely be selected from −270° to 270°.

The signal conversion unit 330 is a general Analog-to-Digital (A/D) converter.

The controller 340 controls the entire system, and is preferably embodied as a microprocessor into which a ROM, a RAM, and peripheral devices are integrated. The controller 340 can identify the cassette 10, detect the injection of a sample solution, or measure the amount of glycated hemoglobin.

That is, by outputting a light-emitting control signal to the light-emitting element and converting an optical signal inputted from the light-receiving element into an electrical signal through A/D converter, whether the first reagent and the second reagent are properly present in the cassette 10 can be detected. In this manner, it is possible to measure the amount of glycated hemoglobin included in the second measurement zone 130 of the cassette 10.

A method in which the separable cassette for measuring glycated hemoglobin 10 according to an embodiment of the present invention can be used comprises a method for measuring glycated hemoglobin comprising the steps of: identifying the information of the engaged cassette 10; confirming whether a first reagent and a second reagent are present in the cassette 10; rotating the cassette 10 in a first direction to leak the first reagent; rotating the cassette 10 to its original state to react the first reagent with a blood sample and measuring an amount of total hemoglobin; rotating the cassette 10 in the first direction to move the blood sample mixture reacted with the first reagent to a second measurement zone 130; rotating the cassette 10 in a second direction to leak the second reagent; rotating the cassette 10 in the first direction to move the second reagent to a second measurement zone 130 and washing the blood sample mixture to measure an amount of glycated hemoglobin; and calculating an amount of glycated hemoglobin in the blood sample based on the measured amount of total hemoglobin and the measured amount of glycated hemoglobin in the blood sample.

Hereinafter, referring to FIGS. 2 to 12, an embodiment of a method for measuring glycated hemoglobin using the separable cassette for measuring glycated hemoglobin 10 according to the present invention will be described in detail.

FIG. 2 is a flowchart illustrating a method of measuring glycated hemoglobin using the cassette 10 according to an embodiment of the present invention. As shown in FIG. 2, a device for measuring glycated hemoglobin 30 identifies the information of the cassette 10 engaged therein (S100).

Then, the device for measuring glycated hemoglobin 30 confirms whether the first reagent and the second reagent are present in the cassette 10 (S110). This can be confirmed by the cassette 10 check sensor 312.

The blood sample collected from the human body may inject directly into the cassette 10 from outside or may be injected through the blood sampling unit 200 according to an embodiment of the present invention, but is not limited thereto.

Then, the device for measuring glycated hemoglobin 30 rotates the cassette 10 in a first direction to leak the first reagent from the first storage zone 210 (S120).

Thereafter, the cassette 10 rotates to its original state, the first reagent is reacted with the blood sample in the first measurement zone 120, and the amount of total hemoglobin is measured (S130). The blood sample and the first reagent react to form a blood sample mixture accordingly. Here, the cassette 10 may be shaken clockwise and counterclockwise for a predetermined period of time, for example, 1 minute, so that the hemolyzed blood sample can sufficiently react with the glycated hemoglobin binding material-beads. This is to induce a blood sample of the blood sampling unit 200 to be hemolyzed out by the first reagent and simultaneously to specifically react with the glycated hemoglobin binding material-beads. When the amount of total hemoglobin in the blood sample is measured, it is preferable to measure the amount of total hemoglobin in the blood sample by the optical reflectometry technique through the optical sensor. Also, the cassette 10 may rotate about 1-5° so that the blood sample mixture can gather closely to the first measurement zone 120 during the measurement.

Then, when the device for measuring glycated hemoglobin 30 rotates the cassette 10 in the first direction, the blood sample is mixed with the first reagent in the first measurement zone 120, the amount of total hemoglobin is measured, and the blood sample mixture which has been reacted with the first reagent moves to the second measurement zone 130 (S140). At this time, non-glycated hemoglobin and the remaining materials except for glycated hemoglobin binding material-beads conjugated with glycated hemoglobin, present in the second measurement zone 130 can be absorbed into the sample absorption unit 150.

Then, the device for measuring glycated hemoglobin 30 rotates the cassette 10 in a second direction to leak the second reagent from the second storage zone 220 (S150).

Then, the device for measuring glycated hemoglobin 30 rotates the cassette 10 in a first direction to move the leaked second reagent to the second measurement zone 130 and washing the blood sample mixture with the second reagent to measure the amount of glycated hemoglobin (S160). Here, as the second reagent containing the washing solution washes the blood sample mixture, non-glycated hemoglobin (Ao) non-specifically present in the blood sample may be removed and absorbed into the sample absorption unit 150 together with the second reagent. As in the case of measuring the amount of total hemoglobin from the blood sample mixture reacted with the first reagent, the amount of glycated hemoglobin in the blood sample may be measured by the optical reflectometry technique through the optical sensor.

Then, the relative amount of glycated hemoglobin in the blood sample is calculated by dividing the measured amount of total hemoglobin into the measured amount of glycated hemoglobin (S170). At this time, the ratio of glycated hemoglobin with total hemoglobin in the blood sample is calculated by the following Equation 1.

$$\text{Glycated Hemoglobin Ratio (\%)} = \text{Glycated Hemoglobin/Total Hemoglobin} \times 100 \quad \text{[Equation 1]}$$

Hereinafter, embodiments of the present invention will be described in detail with reference to the drawings.

Figure 3B:
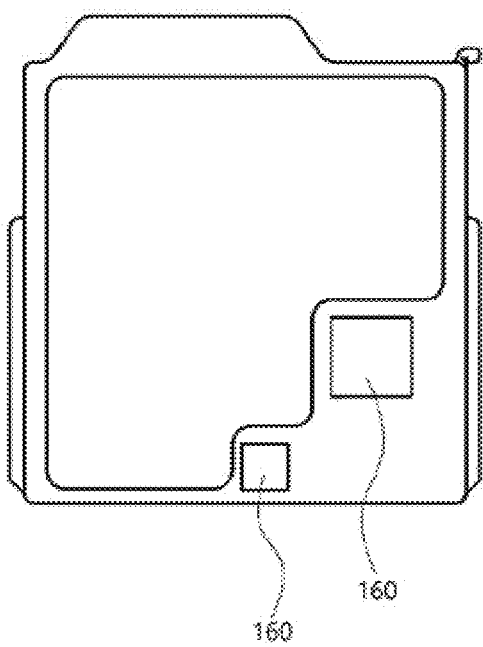

FIG. 3 illustrates (a) an external appearance and (b) an internal appearance of the cassette 10 according to an embodiment of the invention. The cassette 10 of the present invention may be used to measure the amount of glycated hemoglobin (HbA1c) in the blood. At this time, the cartridge 20 can be inserted into the cassette 10, and the cassette 10 is engaged in the device for measuring glycated hemoglobin 30 to be rotatable clockwise or counterclockwise with respect to a horizontal axis. The cassette 10 comprises the removing part 100 in the inlet port for the cartridge 20 insertion so that the leakage preventing unit of the cartridge 20 can be caught and removed when the cartridge 20 is inserted into the device. In addition, the cassette 10 comprises in the interior the insertion guide unit 110 for guiding the cartridge 20 to be inserted into the cassette 10 only in one direction. The cassette 10 further comprises on the bottom of the interior a first measurement zone 120 in which the first reagent reacts with the blood sample and the amount of total hemoglobin is measured, and in the middle of the right side a second measurement zone 130 in which the second reagent washes the reacted blood sample and the amount of glycated hemoglobin is measured. The cassette 10 further comprises on the right side the sample absorption unit 150 which absorbs non-glycated hemoglobin and the remaining materials except for glycated hemoglobin binding material-beads conjugated with glycated hemoglobin. The cassette 10 further comprises on the exterior an optical window 160 from which light received through an external optical sensor is reflected.

Figure 4A:
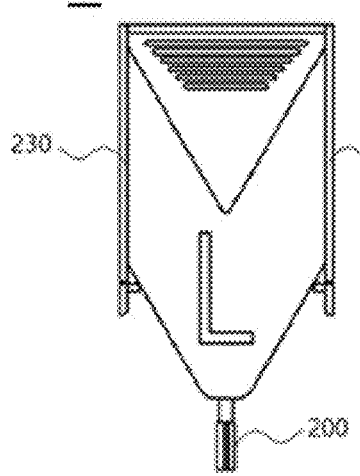
FIG. 4(a), FIG. 4(b), and FIG. 4(c) illustrate a front view, a rear view, and a side view of the cassette, respectively, according to an embodiment of the invention.
Figure 4B:
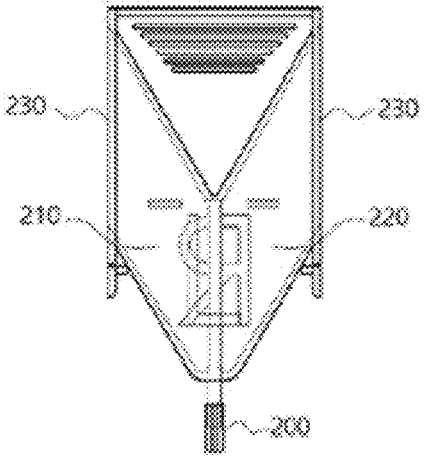
Figure 4C:
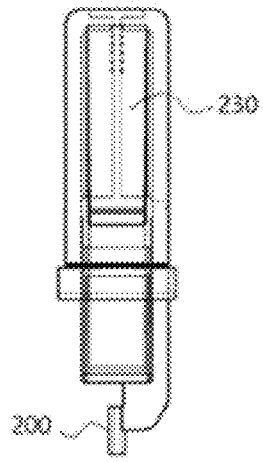

FIG. 4 illustrates (a) a front view, (b) a rear view, and (c) a side view of the cartridge 20 according to an embodiment of the invention. The cartridge 20 comprises a first storage zone 210 for storing a first reagent, a second storage zone 220 for storing a second reagent, a blood sampling unit 200 for collecting, containing and leaking a blood sample, a leakage preventing unit 230 for preventing the first reagent and the second reagent from leaking out until the cartridge 20 is inserted into the cassette 10. The leakage preventing unit 230 is formed on upper side of the cartridge 20, respectively. Since the cartridge 20 has a standing rhombus, even if the leakage preventing unit 230 is removed, the first reagent and the second reagent may be accumulated at the bottom of the cartridge 20 in the rhombus shape. Thus, as long as the cartridge 20 is in its original state without rotating, the reagents do not leak from the storage zones. The leakage preventing unit 230 may be a foil tab.

Figure 5A:
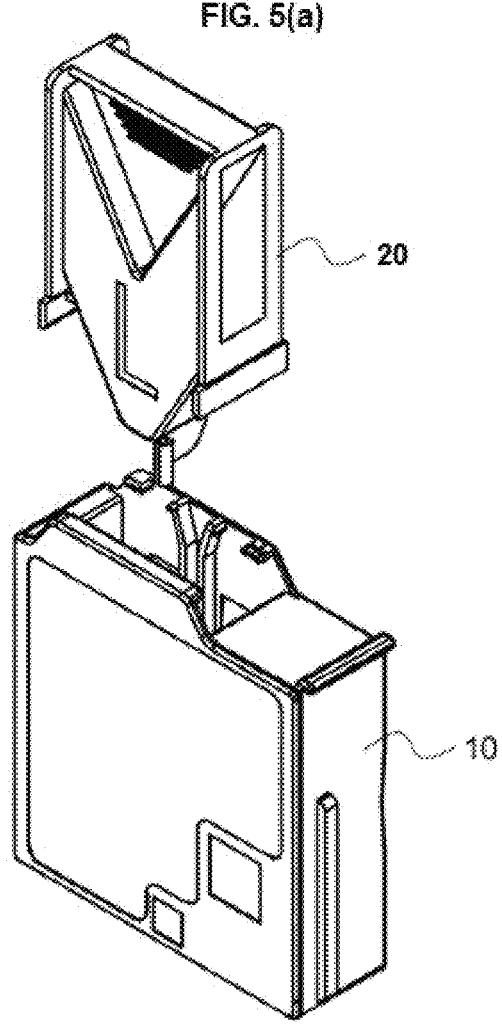
FIG. 5(a) and FIG. 5(b) illustrate the external appearance before and after the cartridge is inserted into the cassette, respectively.
Figure 5B:
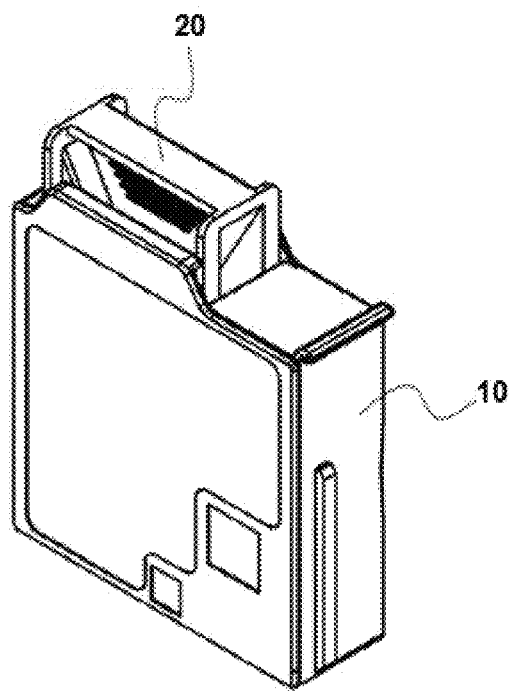

FIG. 5 illustrates the external appearance (a) before and (b) after the cartridge 20 is inserted into the cassette 10. An insertion preventing unit is formed in the cassette 10 so that the cartridge 20 can be inserted only in one direction and the leakage preventing unit 230 of the cartridge 20 can be removed by the removing part 100 of the cartridge 20 at the time of insertion.

Hereinafter, a measuring process of glycated hemoglobin according to the rotation of the cassette 10 into which the cartridge 20 is inserted will be described with reference to FIGS. 6 to 12.

FIG. 6 shows a ready state of the cassette 10 including the first reagent, the second reagent, and the blood sample before rotation. The cartridge 20 is inserted into the cassette 10, the first reagent is contained in the first storage region 210 of the cartridge 20, and the second reagent is contained in the second storage region 220. The leakage preventing unit 230 is caught and removed by removing part 100 when the cartridge 20 is inserted into the cassette 10, and thus is not present. The first reagent and the second reagent do not leak from the storage zones even though the cassette 10 is in its original state without a rotation angle and the leakage preventing unit 230 is not present. Before starting the measurement, the cassette 10 may be shaken for about 30 seconds to allow the reagents in the cassette 10 to mix well.

First, as shown in FIG. 7, the cassette 10 may rotate clockwise by about 65°, whereby the first reagent contained in the first storage zone 210 may leak through the leak hole of the first storage zone 210 by gravity.

Thereafter, as shown in FIG. 8, when the cassette 10 rotates counterclockwise by about 65° to be in its original state, the first reagent moves to the first measurement zone 120 by the delivery guide unit 140. At this time, the blood sample, which is collected from the human body and contained in the blood sampling unit 200, leaks out through the end of the blood sampling unit 200 to react with the first reagent in the first measuring zone 120. In particular, the cassette 10 can be shaken for about 1 minute using device for measuring glycated hemoglobin 30 so that the reaction of the blood sample with the first reagent occurs more easily. At this time, the amount of total hemoglobin in the blood sample can be measured by an optical reflectometry technique through the optical sensor before the reaction is completely finished in the first measurement zone 120.

As shown in FIG. 9, the cassette 10 can rotate clockwise by about 90°, whereby the blood sample reacts with the first reagent in the first measurement zone 120 to measure total hemoglobin, and then the reacted blood sample mixture moves to the second measurement zone 130. At this time, non-glycated hemoglobin and the remaining materials except for glycated hemoglobin binding material-beads conjugated with glycated hemoglobin, present in the second measurement zone 130 can be absorbed into the sample absorption unit 150.

As shown in FIG. 10, when the cassette 10 rotates counterclockwise again by about 155°, it is in a state rotated counterclockwise by about 65° based on its original state, whereby the second reagent may leak through the leak hole of the second storage zone 220 by gravity.

Thereafter, when the cassette 10 rotates clockwise again by about 65° as shown in FIG. 11, and then rotates clockwise by about 90° as shown in FIG. 12, the second reagent moves along the delivery guide unit 140 to the second measurement zone 130 in which the blood sample mixture is present. Next, when the second reagent and the blood sample react, i.e., the second reagent washes the blood sample mixture, the amount of the glycated hemoglobin can be measured from the blood sample mixture from which the non-glycated hemoglobin has been removed. At this time, the amount of glycated hemoglobin in the blood sample may be measured by an optical reflectometry technique through the optical sensor. Non-glycated hemoglobin and the remaining materials except for glycated hemoglobin binding material-beads conjugated with glycated hemoglobin, present in the second measurement zone 130 can be absorbed into the sample absorption unit 150.

In summary, as shown in FIGS. 6 to 12, the device for measuring glycated hemoglobin 30 can automatically rotate the cassette 10 clockwise or counterclockwise. That is, the first reagent or the second reagent leaks sequentially from the first storage zone 210 or the second storage zone 220 according to the rotation of the cassette 10 to react with the blood sample. That is, at least one reagent automatically reacts with the blood sample according to the rotation. In addition, FIGS. 6 to 12 are one example showing the rotation process of the cassette 10 and various other rotations can be embodied. In the case of the embodiments in which each zone of the cassette 10 is positioned symmetrically compared to the above-described embodiments, the cassette 10 can rotate in a manner opposite to the above-described rotation process.

The present invention has been described with reference to the preferred embodiments. However, it will be understood by those skilled in the art that various changes and modifications may be made in the present invention without departing from the spirit or scope of the invention. Accordingly, the disclosed embodiments should be considered as being exemplary and not limiting. The scope of the invention is defined in the claims rather than the detailed description, and all differences within the equivalent range should be interpreted as being included in the invention.

DESCRIPTION OF SYMBOLS

10: Cassette
20: Cartridge
30: Device for measuring glycated hemoglobin
100: Removing part
110: Insertion guide unit
120: First measurement zone
130: Second measurement zone
140: Delivery guide unit
150: Sample absorption unit
160: Optical window
200: Blood sampling unit
210: First storage zone
220: Second storage zone
230: Leakage preventing unit
300: Cassette accommodation part
312: Cassette check sensor
314: Measurement sensor
320: Driving unit
330: Signal conversion unit
340: Controller

The invention claimed is:

1. A device for measuring glycated hemoglobin, comprising:
   a separable cassette,
   a cassette accommodation part configured to accommodate the cassette, and
   a driving unit configured to apply an external power to the cassette,
   wherein the separable cassette comprises:
   a cartridge which includes a first storage zone for storing a first reagent, a second storage zone for storing a second reagent, and a blood sampling unit capable of injecting a blood sample into the cassette, the cartridge being configured to be inserted into the cassette, wherein the blood sampling unit is integrally formed with the cartridge and is located between the first storage zone and the second storage zone to divide an inner space within the cartridge into the first storage zone and the second storage zone;
   an insertion guide unit for guiding an insertion direction when the cartridge is inserted into the cassette and located between the first storage zone and the second storage zone;
   a first measurement zone in which the blood sample reacts with the first reagent to measure an amount of total hemoglobin; and
   a second measurement zone in which the reacted blood sample reacts with the second reagent to measure an amount of glycated hemoglobin,
   wherein the driving unit is configured to rotate the cassette by applying the external power such that, as the cassette rotates by a first predetermined angle or more relative to a horizontal axis of the cassette in a first direction, the first reagent leaks from the first storage zone and moves to the first measurement zone, or as the cassette rotates by a second predetermined angle or more relative to the horizontal axis of the cassette in a second direction opposite to the first direction, the second predetermined angle being opposite to the first predetermined angle, the second reagent leaks from the second storage zone and moves to the second measurement zone, and
   wherein the cassette further comprises:
   a first leakage hole, which is a passage through which the first reagent leaks out, the first leakage hole being provided on an upper side of the first storage zone; and
   a second leakage hole, which is a passage through which the second reagent leaks out, the second leakage hole being provided on an upper side of the second storage zone, the first leakage hole and the second leakage hole being opposite to each other with respect to the insertion guide unit.

2. The device for measuring glycated hemoglobin according to claim 1, wherein, in the cartridge that is inserted into the cassette, the first storage zone is located closer to the first measurement zone and the second measurement zone than the second storage zone.

3. The device for measuring glycated hemoglobin according to claim 2, wherein the first measurement zone is located at a lower level than the second measurement zone.

4. The device for measuring glycated hemoglobin according to claim 1, wherein the cartridge further comprises a leakage preventing unit which is disposed at one end of the first storage zone and the second storage zone, respectively, to prevent the first reagent and the second reagent from leaking out, and is removed from the cartridge when the cartridge is inserted into the cassette.

5. The device for measuring glycated hemoglobin according to claim 4, wherein the leakage preventing unit is removed by a removing part which is disposed in an inlet port of the cassette.

6. The device for measuring glycated hemoglobin according to claim 1, wherein the first reagent leaks from the first storage zone when the cassette rotates I 0-130° in the first direction based on the horizontal axis of the cassette.

7. The device for measuring glycated hemoglobin according to claim 1, wherein the second reagent leaks from the second storage zone when the cassette rotates 10-130° in the second direction based on the horizontal axis of the cassette.

8. The device for measuring glycated hemoglobin according to claim 1, wherein the cassette further comprises a delivery guide unit for guiding for the blood sample, the first reagent, or the second reagent, to move to the first measurement zone or the second measurement zone.

9. The device for measuring glycated hemoglobin according to claim 1, wherein the cassette further comprises a sample absorption unit which is located at one end of the second measurement zone to absorb the measured blood sample and sample.

10. The device for measuring glycated hemoglobin according to claim 1, wherein the cassette further comprises an optical window from which light received from an external optical sensor is reflected.

* * * * *